US009682217B2

(12) United States Patent
Franklin et al.

(10) Patent No.: US 9,682,217 B2
(45) Date of Patent: Jun. 20, 2017

(54) VASCULAR ACCESS SYSTEMS AND METHODS OF USE

(71) Applicant: Prytime Medical Devices, Inc, Boerne, TX (US)

(72) Inventors: Curtis Franklin, Denver, CO (US); Jonathan L. Eliason, Ann Arbor, MI (US)

(73) Assignee: PRYTIME MEDICAL DEVICES, INC., Boerne, TX (US)

( * ) Notice: Subject to any disclaimer, the term of this patent is extended or adjusted under 35 U.S.C. 154(b) by 265 days.

(21) Appl. No.: 14/191,236

(22) Filed: Feb. 26, 2014

(65) Prior Publication Data

US 2014/0249504 A1    Sep. 4, 2014

Related U.S. Application Data

(60) Provisional application No. 61/769,664, filed on Feb. 26, 2013.

(51) Int. Cl.
*A61M 25/06* (2006.01)
*A61M 5/158* (2006.01)

(52) U.S. Cl.
CPC ............ *A61M 25/06* (2013.01); *A61M 5/158* (2013.01); *A61M 25/065* (2013.01); *A61M 2005/1585* (2013.01); *A61M 2005/1586* (2013.01)

(58) Field of Classification Search
CPC .. A61M 2005/1585; A61M 2005/1586; A61M 25/06; A61M 25/065; A61M 5/158
See application file for complete search history.

(56) References Cited

U.S. PATENT DOCUMENTS

| 3,964,482 | A | 6/1976 | Gerstel et al. ................ 128/260 |
| 5,611,809 | A | 3/1997 | Marshall et al. |
| 2002/0045850 | A1 | 4/2002 | Rowe et al. .................... 604/22 |
| 2003/0199823 | A1* | 10/2003 | Bobroff ................. A61M 5/158 604/136 |
| 2003/0208167 | A1 | 11/2003 | Prausnitz et al. ............ 604/272 |
| 2003/0229317 | A1 | 12/2003 | Ferguson et al. ............ 604/263 |
| 2010/0312173 | A1 | 12/2010 | McKay et al. |
| 2015/0246214 | A1* | 9/2015 | Simmers ........... A61M 37/0015 604/506 |

FOREIGN PATENT DOCUMENTS

| FR | 2448337 | * 2/1979 | ............... A61B 5/15 |
| KR | 10-2004-0022824 | 3/2004 | ........... A61M 5/178 |
| WO | 9322971 A1 | 11/1993 | |

OTHER PUBLICATIONS

International Search Report issued in corresponding foreign application, PCT/US2014/018773, pp. 1-8 (May 7, 2014).
Written Opinion issued in corresponding foreign application, PCT/US2014/018773, pp. 1-7 (May 7, 2014).
Int'l Preliminary Report on Patentability issued Sep. 1, 2015 in Int'l Application No. PCT/US2014/018773.
Extended Search Report issued Sep. 9, 2016 in EP Appln No. 14756921.4.

* cited by examiner

*Primary Examiner* — Imani Hayman
(74) *Attorney, Agent, or Firm* — Panitch Schwarze Belisario & Nadel LLP

(57) ABSTRACT

A vascular access system and method of use for said system. The vascular access system generally comprises a body member; a shuttle member movably coupled to the body member; and a plurality of access needles fixedly coupled to the shuttle member and extending from the body member to penetrate a patient's skin.

20 Claims, 11 Drawing Sheets

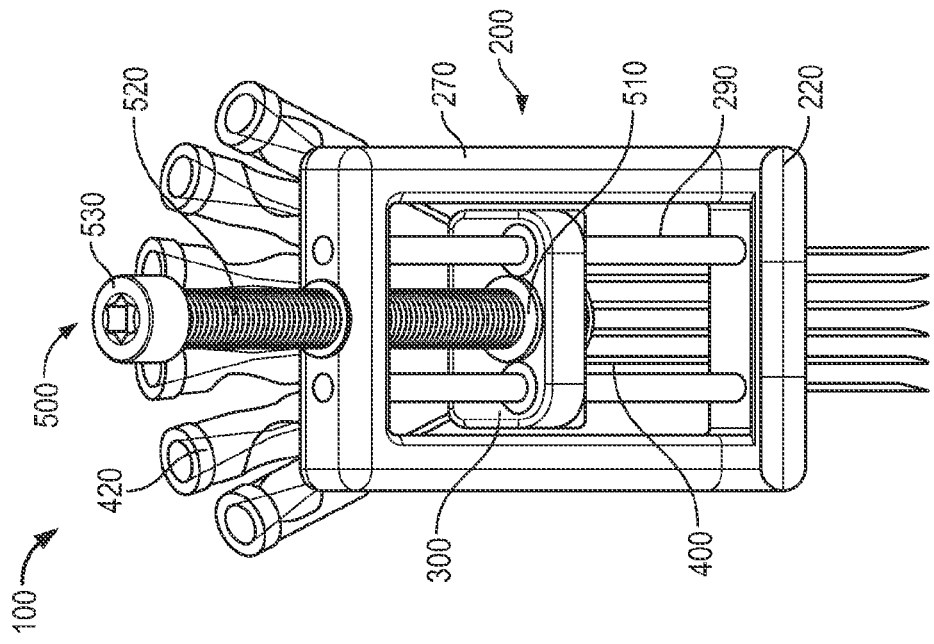
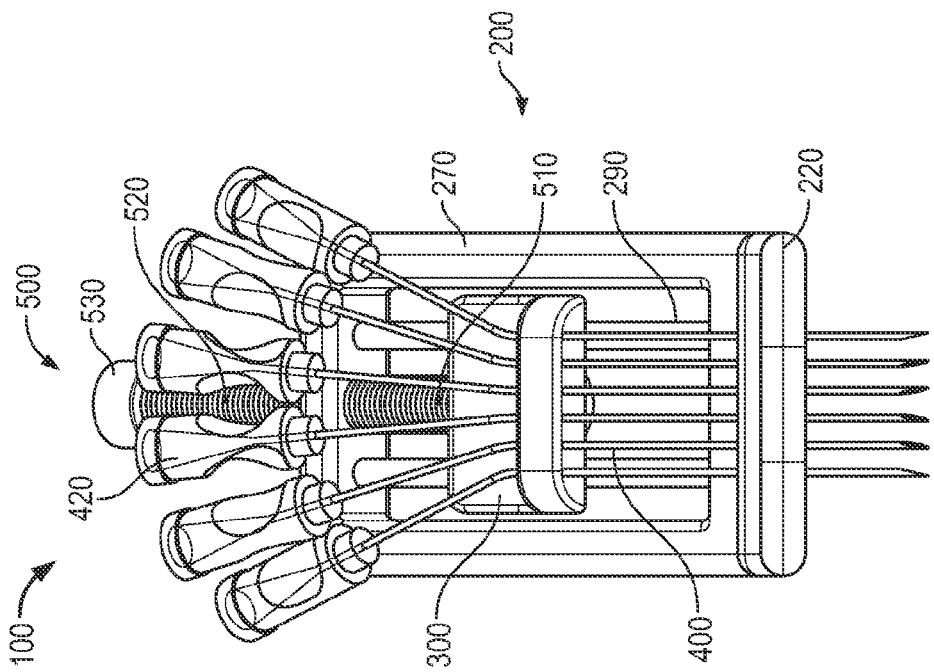
FIG. 2
FIG. 3

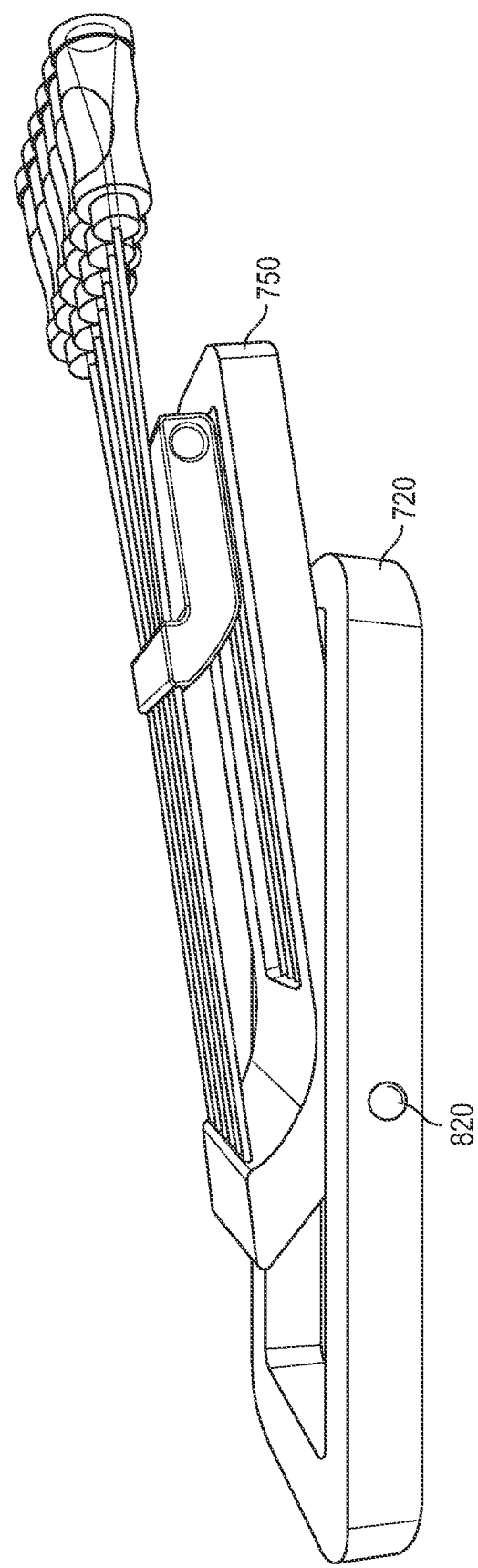

VASCULAR ACCESS SYSTEMS AND METHODS OF USE

CROSS-REFERENCE TO RELATED APPLICATIONS

The present application claims priority from U.S. Provisional Patent Application Ser. No. 61/769,664, filed on Feb. 26, 2013, which is hereby incorporated in its entirety.

STATEMENT REGARDING FEDERALLY SPONSORED RESEARCH OR DEVELOPMENT

This invention was made with government support under Contract No. W81XWH-14-1-0601awarded by the U.S. Army Medical Research and Materiel Command. The government has certain rights in the invention.

BACKGROUND

The invention generally relates to systems and methods for vascular access. More particularly, the invention relates to systems and methods for assisting medical practitioners in achieving vascular access in a rapid and consistent manner.

Typically, blood vessels or other hollow organs are accessed by practicing the Seldinger technique. In the Seldinger technique, the desired vessel or cavity is punctured with a sharp hollow needle called a trocar, with ultrasound guidance if necessary. A round-tipped guidewire is then advanced through the lumen of the trocar, and the trocar is withdrawn. A "sheath" or blunt cannula can then be passed over the guidewire into the cavity or vessel. After passing a sheath or tube, the guidewire is withdrawn. Vascular access, such as through the Seldinger technique, is generally not practiced outside of controlled hospital environments, and is generally not suitable to uncontrolled environments.

Paramedics, military medics, and other medical professionals who typically practice in field settings rather than clinic or hospital settings generally do not have available ultrasound systems or other external guidance systems for assisting with vascular access. Even trained vascular surgeons may require ultrasound assistance to properly access the vessel for guidewire placement. Still further, medical professionals in the field or other settings may experience conditions where practicing standard vascular access techniques, such as the Seldinger technique, may be impractical or impossible.

The present invention seeks to solve this problem, and others.

SUMMARY OF THE INVENTION

Provided herein are systems and methods of use for a vascular access system.

Generally speaking, the vascular access system of the present invention is a system for providing vascular access rapidly and without the need for additional monitoring/guidance systems, such as an ultrasound system. With the inventive vascular access system, vascular access may be achieved by medical professionals in the field or other settings where conditions for practicing standard vascular access techniques, such as the Seldinger technique, may be impractical or impossible.

In one embodiment, the vascular access system comprises a body member, a shuttle member movably coupled to the body member, and a plurality of parallel access needles fixedly coupled to the shuttle member. The plurality of needles may be evenly spaced from one another (center of needle to center of needle), and provide optimized lateral spanning of the region of a desired blood vessel (such as the femoral artery). The body member is adapted to be held against the skin of a patient in the general area of a desired blood vessel, and holds the shuttle member and access needles at a set angle relative to the skin, to enhance proper vascular access. The shuttle member may be advanced in a controlled manner by a medical professional such that the access needles simultaneously and evenly penetrate the skin of the patient. The shuttle may be advanced by the medical professional until aspiration of blood sufficient to indicate vascular access is observed from at least one of the access needles. If more than one needle is aspirating blood, the needle aspirating the most blood has likely accessed a large artery, e.g., the femoral artery. Less aspiration would likely be noted in a vein or a smaller artery. A guidewire may then be fed through the aspirating needle and into the blood vessel. The vascular access system may then be removed while maintaining the position of the guidewire. The desired blood vessel is thus accessed and ready to have a catheter, sheath, occlusion device, second wire, or other medical device inserted therein, as necessary. By use of the inventive vascular access system, vascular access may rapidly, safely, and repeatedly be achieved, without the need for additional monitoring or guidance systems. As such, vascular access may be achieved by medical professionals in the field or other settings where conditions for practicing standard vascular access techniques, such as the Seldinger technique, may be impractical or impossible.

In another embodiment there is disclosed, in accordance with the present invention, a vascular access system, comprising: a body member; a shuttle member movably coupled to the body member; a plurality of access needles fixedly coupled to the shuttle member; and a control assembly operably coupled to the body member and the shuttle member, wherein the control assembly is adapted to provide a controlled rate of advancement of the shuttle member relative to the body member.

Generally, a method of vascular access comprises the steps of: 1) placing a vascular access system over an estimated location of a desired blood vessel of a patient; 2) advancing a plurality of access needles such that the plurality of access needles penetrate the tissue of the patient in the estimated location of the desired blood vessel; 3) observing an aspiration of blood from at least one of the needles, indicating said needle has accessed the desired blood vessel; 4) inserting a guidewire through the said needle and into the desired blood vessel; and 5) removing the vascular access system while maintaining the position of the guidewire.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

FIG. 2 is a front view of the embodiment of FIG. 1.

FIG. 3 is a back view of the embodiment of FIG. 1.

FIG. 13 is a perspective view of the example embodiment shown in FIG. 11 configured at a different angle, α.

DETAILED DESCRIPTION OF THE INVENTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

In the following description, the terms "distal" and "proximal" are intended to be spatial orientation descriptors relative to the longitudinal axis of the vascular access assembly. Thus, a "proximal" side refers to a side of an element generally facing a medical professional and away from the patient and, conversely, a "distal" side refers to a side of an element generally facing away from the medical professional and toward the patient. Likewise a pair of elements described as "proximal" and "distal" elements are understood to have the same spatial relationship as described hereinabove for the sides of an element.

Generally speaking, the vascular access system of the present invention is a system for providing vascular access safely, rapidly, and repeatably, without the need for additional monitoring/guidance systems, such as an ultrasound system. With the inventive vascular access system, vascular access may be achieved by medical professionals in the field or other settings where conditions for practicing standard vascular access techniques, such as the Seldinger technique, may be impractical or impossible.

Figure 8:
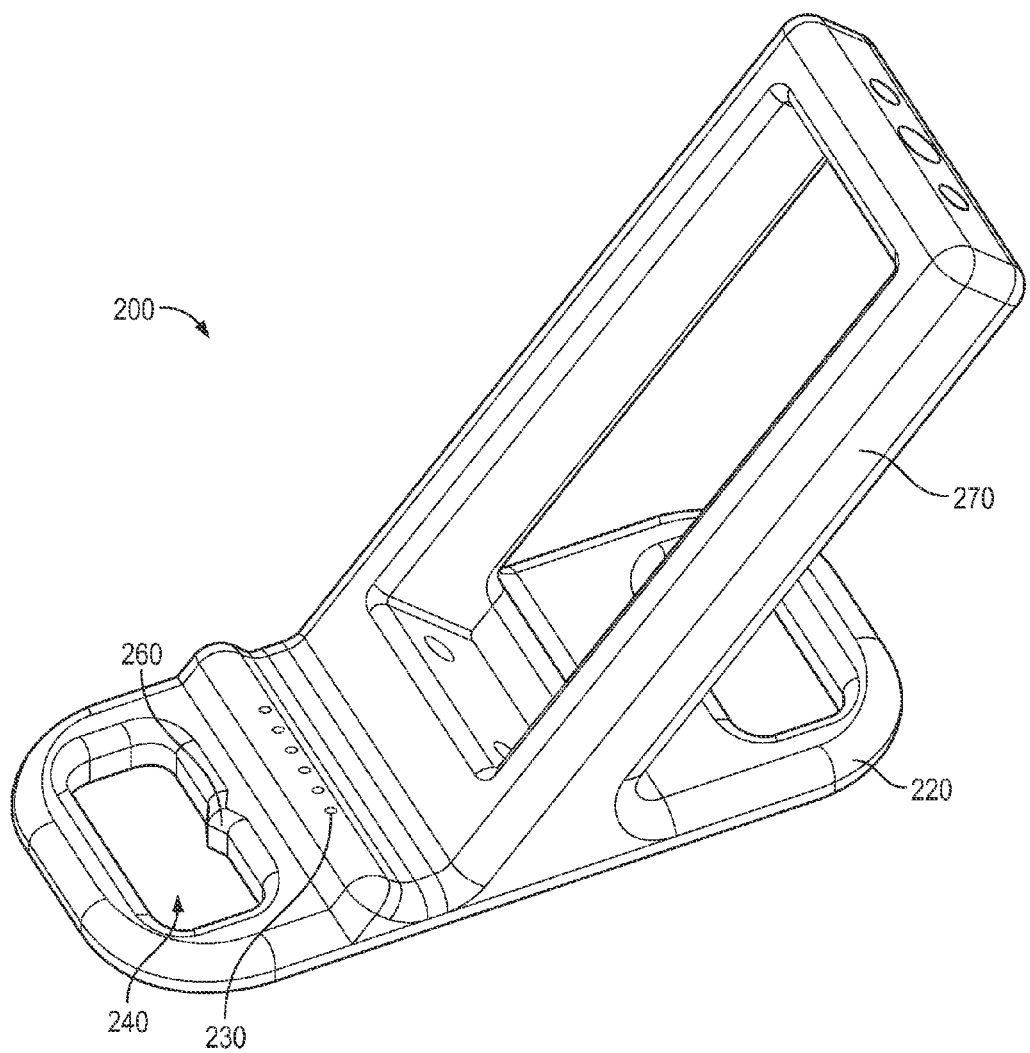
FIG. 8 is an isometric view of the body member of the embodiment of FIG. 1.

In one embodiment, illustrated in FIGS. 1-7, the vascular access system 100 comprises a body member 200, a shuttle member 300 is movably coupled to a portion of the body member 200, and a plurality of parallel access needles 400 are fixedly coupled to the shuttle member 300 and pass through apertures or guides 230 (depicted in FIG. 8) associated with another portion of the body member 200. The plurality of needles extend from an upper portion of the body member and pass through to and extend beyond a lower portion of the body member 200. The plurality of needles 400 are evenly spaced from one another (center of needle to center of needle), and provide optimized lateral spanning of the region of a desired blood vessel (such as the femoral artery). The body member 200 is adapted to be held against the skin of a patient in the general area of a desired blood vessel, such that the lower portion of the body member 200 is adjacent the patient's skin, the upper portion of the body member 200, the shuttle member 300 and access needles 400 are positioned at a predetermined angle relative to the skin, to achieve proper vascular access by the needles being advanced and penetrating the patient's skin. The shuttle member 300 may be advanced in a controlled manner by a medical professional such that the access needles 400 simultaneously and evenly penetrate the skin of the patient. The shuttle member 300 may be advanced by the medical professional until aspiration of blood sufficient to indicate vascular access is observed from at least one of the access needles 400. If more than one needle 400 is aspirating blood, the needle 400 aspirating the most blood has likely accessed a large artery, e.g., the femoral artery. Less aspiration would likely be noted in a vein or a smaller artery. A guidewire may then be fed through the aspirating needle 400 and into the blood vessel. The vascular access system 100 may then be removed while maintaining the position of the guidewire. The desired blood vessel is thus accessed and ready to have a catheter, sheath, occlusion device, second wire, or other medical device inserted therein, as necessary. By use of the inventive vascular access system 100, vascular access may rapidly, safely, and repeatedly be achieved, without the need for additional monitoring or guidance systems. As such, vascular access may be achieved by medical professionals in the field or other settings, where conditions for practicing standard vascular access techniques, such as the Seldinger technique, may be impractical or impossible.

In some embodiments, as illustrated in FIGS. 1-8, the body member 200 comprises a base member 220 and a stand member 270. The base member 220 and the stand member 270 may be coupled together or integrally formed at a fixed angle, α. The angle α is preferably 45 degrees, but may be any other angle that permits vascular access by the access needles 400 and insertion of guidewire into the blood vessel through the access needles 400. In one embodiment, the angle α is between about 30 degrees and about 60 degrees. Additionally, the base member 220 may further comprise needle apertures 230 configured such that the needles 400 may freely translate through said apertures 230 as the shuttle 300 and needles 400 are advanced.

The base member 220 is adapted to be have a lower surface of the base member placed or held against the skin of a patient, the needles passing through the plane of the lower surface and penetrating into the patient's skin. In some embodiments, the base member 220 may further comprise at least one window or open portion 240. In a preferred embodiment, the base member 220 has two windows 240, which may optionally be located on either side of the stand member 270. In a further embodiment, the base member 220 may further comprise an alignment element 260, such as an alignment nub 260. In some embodiments, the alignment nub 260 may be disposed within a window 240 in the base member 220. The alignment element 260 is aligned with a centrally located access needle 400, such that the center needle 400 may be aligned with the estimated location of the desired blood vessel. The alignment element 260 may be used to align the vascular access system 100 with landmarks for the desired blood vessel that have been identified by the medical professional. Landmarks may comprise bony markers, marks made on the patient's skin by the medical professional, and/or the like. In one embodiment, the general location of a desired blood vessel is determined by the medical professional checking for a pulse, such as on the femoral artery, radial artery, and/or the like. The vascular access system 100 permits rapid, safe, and repeatable achievement of vascular access, without the need for additional monitoring systems or extensive expertise, or in settings where conditions for practicing standard vascular access techniques, such as the Seldinger technique, may be impractical or impossible.

The plurality of access needles 400 are configured such that a guidewire may be disposed through said needles. In one particular embodiment, the access needles 400 are 21 gauge. In other embodiments, the needles 400 may be any gauge sufficient to permit a guidewire to be disposed there through. In still other embodiments, the needles 400 may be sized to permit other medical devices to be disposed there through.

The plurality of parallel access needles 400 are held in a fixed spacing relative to each other by the shuttle member 300. This fixed spacing provides optimized lateral spanning of the region of a desired blood vessel (such as the femoral artery). In one embodiment, the plurality of parallel access needles 400 are spaced apart from one another, measured from the center of a first needle 400 to the center of a second needle 400, by a distance of about 3 mm. Alternatively, the needle spacing may be about 4 mm or about 5 mm or any spacing that is desired and achieves optimized vascular access. Generally, the spacing is any distance such that the probability is optimized that one of the plurality of access needles 400 will obtain access to the desired blood vessel.

The plurality of parallel access needles 400 may comprise any appropriate number of needles 400, such that the necessary lateral span is covered by the needles. In a preferred embodiment, the number of needles 400 is five. In additional embodiments, the number of needles 400 could be 3, 4, 6, 7, and/or the like. In some embodiments, a middle or central needle 400 may be aligned with the alignment element 260. In some embodiments, at least one of the plurality of parallel access needles 400 may further comprise a needle hub element 420, where the hub element 420 improves the ease of guidewire insertion through said at least one needle 400 once the desired blood vessel is accessed.

Figure 9:
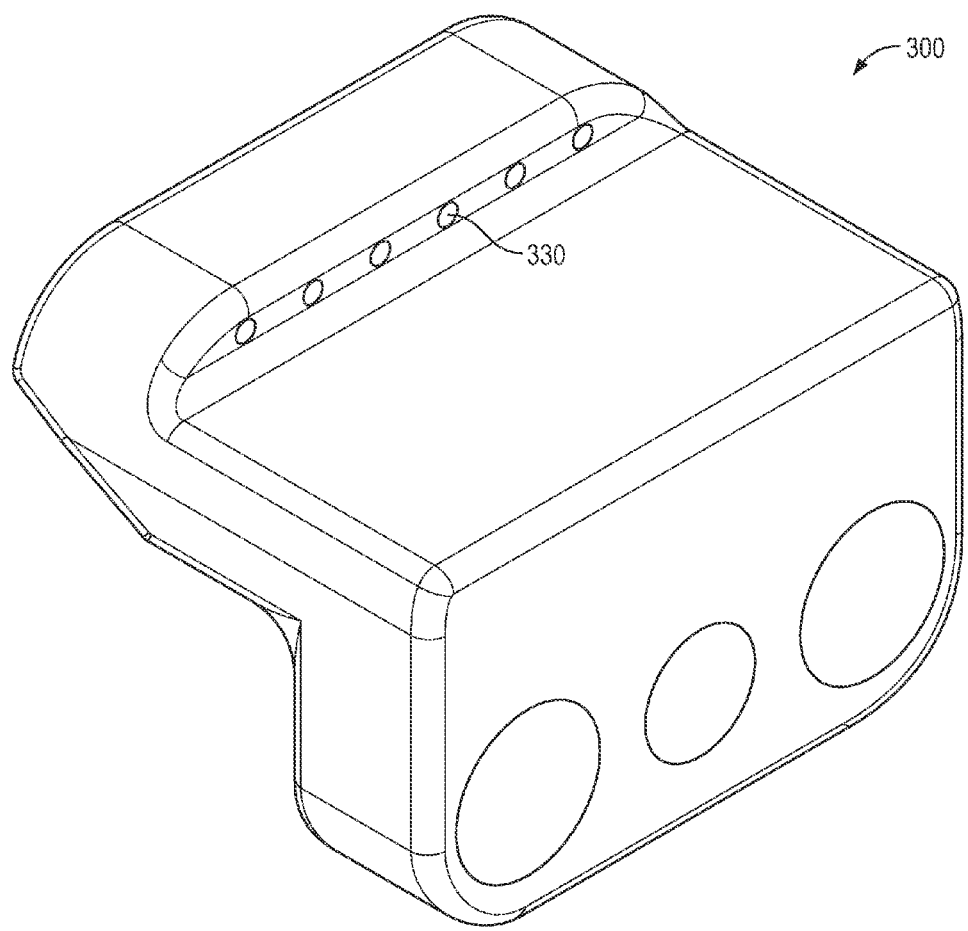
FIG. 9 is an isometric view of the shuttle member of the embodiment of FIG. 1.

One embodiment of the shuttle member 300 of the present invention is illustrated in FIG. 9. The plurality of needles 400 may be fixedly coupled to the shuttle member 300 in any manner known in the art, such that the needles 400 are fixed relative to the shuttle 300. The shuttle member 300 may further comprise a plurality of needle apertures 330, configured such that the needles 400 may be disposed through the apertures 330 and then fixed in position. This fixation may be by any appropriate means, such as glue, weld, integral formation, and/or the like, so long as the needles 400 are fixed in position relative to the shuttle 300.

The vascular access system 100 may be formed of any appropriate material. In a preferred embodiment, the body member 200 and shuttle member 300 may comprise injection molded plastic. In other embodiments, the body member 200 and shuttle member 300 may comprise metal, plastic, and/or the like.

Generally, the present invention requires only that the advancement of the shuttle and access needles be in a controlled manner. The shuttle member 300 is movably coupled to and moveable substantially axially relative to the body member 200 to drive the plurality of needles 400 into the subject. In some embodiments, the shuttle member 300 is slidably coupled to the stand member 270, the sliding engagement between the shuttle member and the stand member may be controlled, at least in part, by a frictional relationship, interference relationship, detents, threads, or the like.

In another embodiment, the body member 200 further comprises rail members 290, such that the shuttle member 300 is slidably coupled to the rail members 290. In some embodiments, the advancement of the shuttle 300 along the rails 290 may be controlled by a frictional relationship between the rails 290 and the shuttle 300, but may also be controlled by interference fit, detents, threads or the like.

In another embodiment, illustrated in FIGS. 1-7, the shuttle 300 and body member 200 may be operably coupled to a control assembly 500, wherein said control assembly 500 provides a controlled rate of advancement of the shuttle member 300 relative to the body member 200. In one embodiment, the control assembly 500 may comprise a screw drive system. The screw drive system may comprise a threaded shaft 520 having proximal end 530 and distal end 510, wherein the distal end 510 is coupled to the shuttle 300 and the proximal end 530 terminates in a knob or handle member adapted to be rotated by the medical professional to advance or withdraw the shuttle 300 and needles 400. The stand member 270 further comprises a threaded aperture 525, through which the threaded shaft 520 is disposed. The distal end 510 of the threaded shaft 520 may be coupled to the shuttle 300 such that the threaded shaft 520 may rotate independent of the shuttle 300, while the shuttle 300 is advanced or withdrawn by the rotation of the shaft 520. In one embodiment, the coupling may comprise nuts or lock nuts 550 disposed on the shaft 520 adjacent both sides of the shuttle 300. In an alternative embodiment, the screw drive system may further comprise a gearing mechanism to alter the proportional relationship between the rotation of the knob at the proximal end 530 of the threaded shaft 520 and the advancement or withdrawal of the shuttle 300 and needles 400. As such, the gearing mechanism may be adapted to increase the distance which the shuttle 300 and needles 400 are advanced per complete rotation of the knob or handle.

Figure 10:
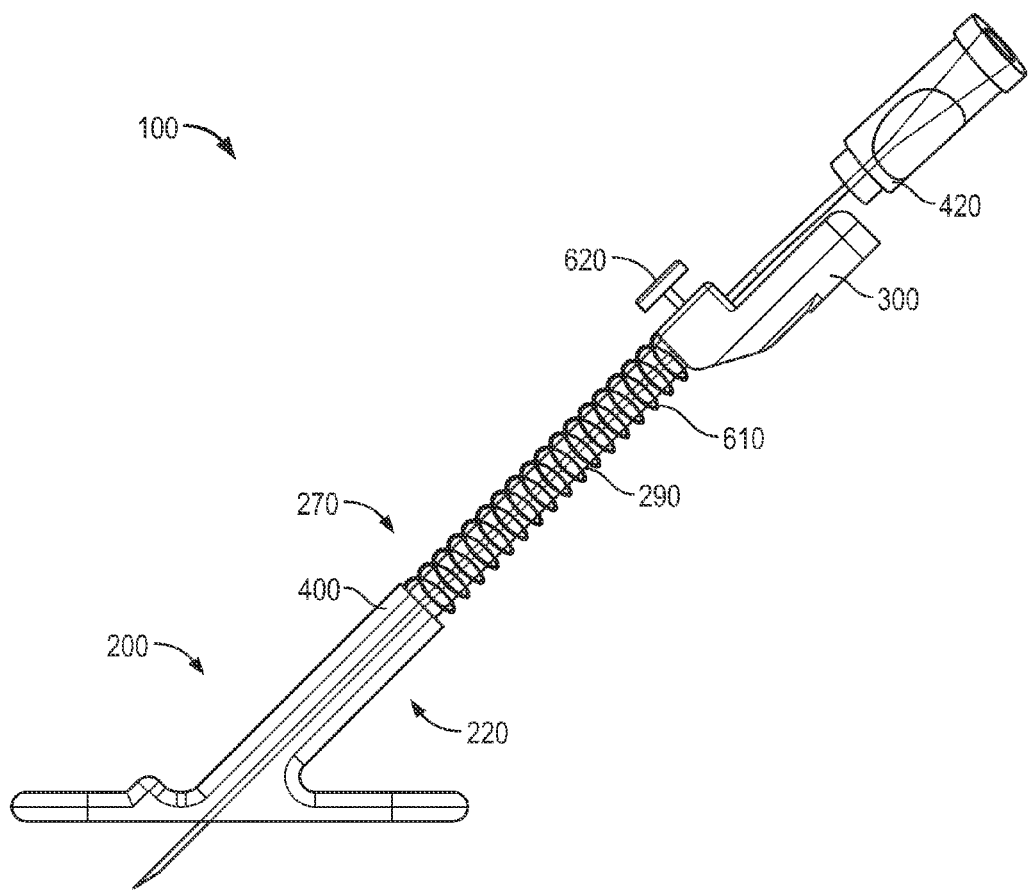
FIG. 10 is an illustration of an embodiment of the vascular access system of the present invention further comprising a spring loaded ratcheting system.

In another embodiment, illustrated in FIG. 10, the control assembly 500 may comprise a ratchet assembly. The ratchet assembly may comprise a spring loaded ratcheting system. The spring loaded ratcheting system may comprise a tension spring 610 operably coupled to the shuttle 300 and the body member 200, and an advancement mechanism 620 operably coupled to the shuttle 300 and the body member 200. The body member 200 may further comprise a plurality of rails 290. In operation, the shuttle 300 and needles 400 may be advanced by operating the advancement mechanism 620 such that that tension spring 610 pulls the shuttle 300 and needles 400 forward. The advancement mechanism 620 may permit incremental advancement of the shuttle 300 and needles 400, where each increment is a small and precise distance. As such, a medical professional may advance the shuttle 300 and needles 400 in small increments until one of the needles 400 penetrates into the desired blood vessel and blood aspiration through the particular needle 400 is observed. In some further embodiments, the advancement mechanism 620 may comprise a lever assembly operable to permit incremental advancement of the shuttle 300 and needles 400. In an alternative embodiment, the ratchet assembly may comprise a tension member operably coupled to the shuttle member 300 and the body member 200, and an activator mechanism, wherein the activator mechanism permits a controlled, incremental advancement of the shuttle member 300.

In still further embodiments, the control assembly 500 may comprise: a geared control assembly; a rack and pinion system; a frictional slide and rail assembly; and/or like systems to permit advancement of the shuttle 300 and needles 400 at a controllable rate. Control of the rate of advancement of the shuttle 300 and needles 400 is necessary to prevent advancement of the needles 400 completely through the desired blood vessel.

Those skilled in the art will understand and appreciate that other control mechanisms may be employed to permit advancement of the shuttle 300 and needles 400 at a controlled or controllable rate relative to the body member 200, including, without limitation, plungers, syringe-like mechanisms, or single rail, dual rail, triple rail or other multiple rail configurations of the body member 300 and shuttle 300 may be employed, consistent with the foregoing examples.

In an additional embodiment of the present invention, there is a vascular access system, comprising: a body member; a shuttle member movably coupled to the body member; a plurality of access needles fixedly coupled to the shuttle member; and a control assembly operably coupled to the body member and the shuttle member, wherein the control assembly is adapted to provide a controlled rate of advancement of the shuttle member relative to the body member.

Figure 11:
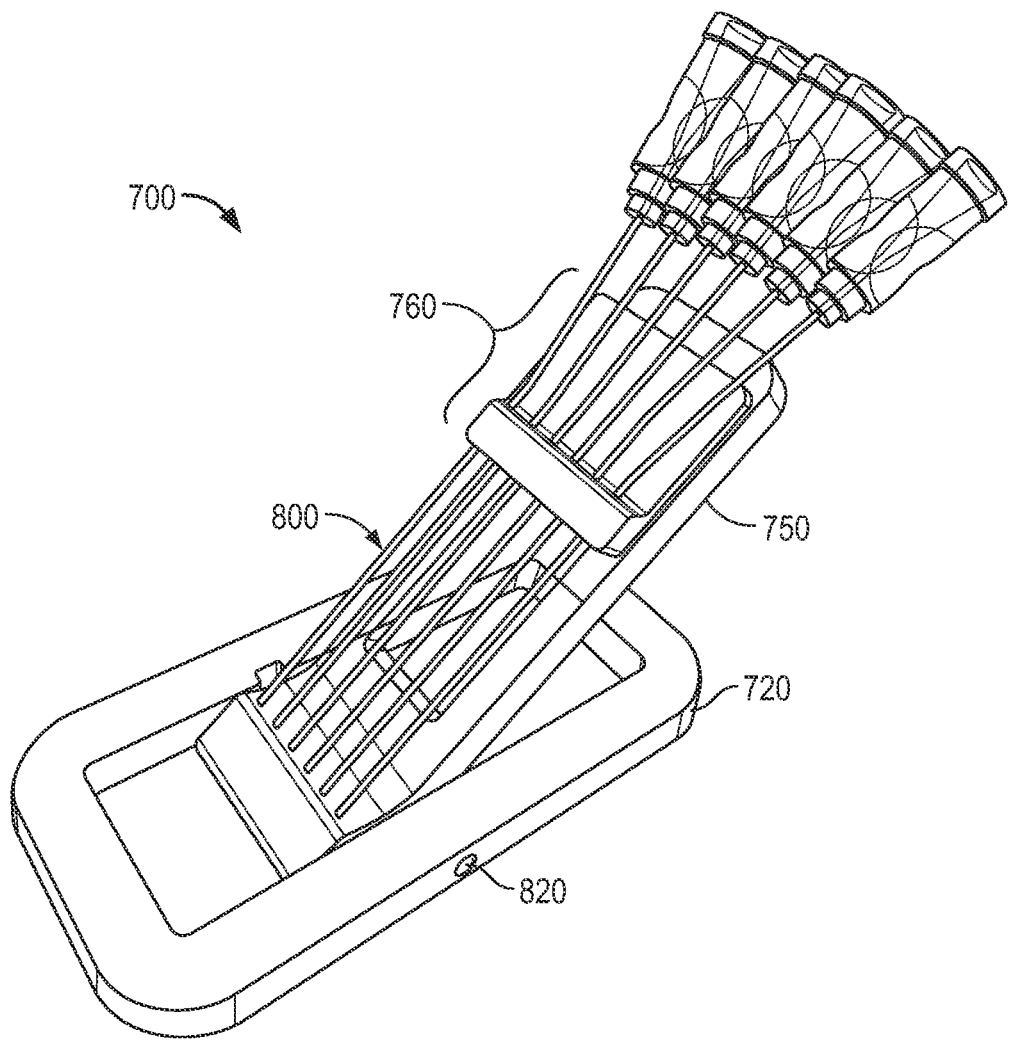
FIG. 11 is a perspective view of another example of an embodiment of a vascular access system.
Figure 12A:
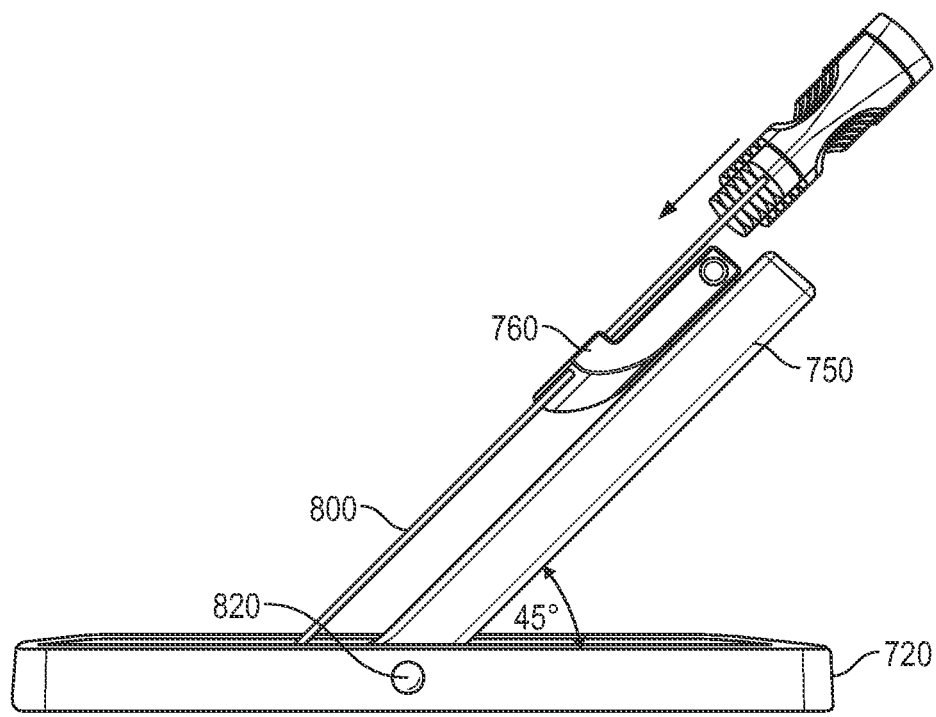
FIGS. 12A and 12B are side views of the example embodiment shown in FIG. 11 illustrating operation of the vascular access system.
Figure 12B:
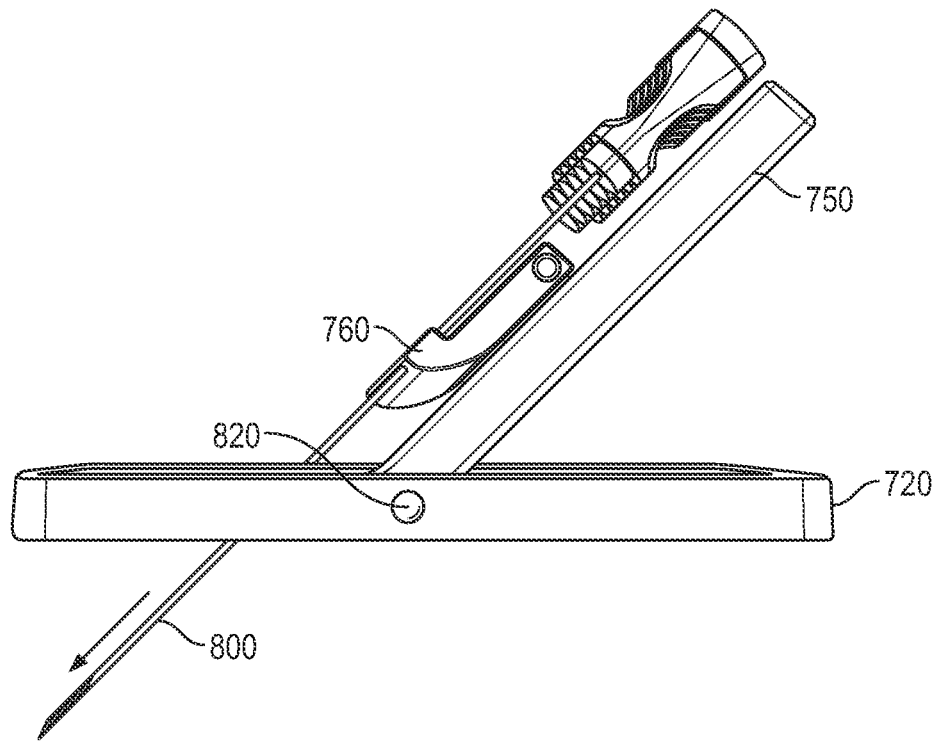

In another embodiment, no control mechanism is employed in the vascular access system leaving control of the advancement of the needles to the operator of the system. An example of an embodiment with no added control mechanism is illustrated in FIGS. 11-13. The example embodiment illustrated in FIGS. 11-13 also permits adjusting the standing member relative to the body member at a variable angle, α. FIG. 11 is a perspective view of an example embodiment of a vascular access system 700 in which no control mechanism. FIGS. 12A and 12B are side views of the example embodiment shown in FIG. 11 illustrating operation of the vascular access system 700. FIG. 13 is a perspective view of the example embodiment shown in FIG. 11 configured at a different angle, α.

Referring to FIG. 11 the example vascular access system 700 includes a base member 720, a standing member 750, a shuttle member 760, a plurality of vascular access needles 800, and a pivot member 820. The shuttle member 760 may be movably attached to the standing member 750 using a rail or any other suitable mechanism as described above with reference to FIGS. 1-10. As shown in FIG. 11, the shuttle member 760 is not attached to any control mechanism that would provide control over the advancement of the shuttle member 760 and access needles 800. As shown in FIG. 12A, the operator is in control of the advancement of the shuttle member 760 and needles 800 by applying a force on the shuttle member 760 along a desired angle α. The angle α in the example shown in FIGS. 12A & 12B is 45°. As shown in FIG. 12B, the needles 800 have been advanced along the angle α=45°.

The operator may vary the angle α by moving the standing member 750 relative to the base member 720 around the pivot member 820. FIG. 13 illustrates the standing member 750 positioned relative to the base member 720 at an angle much less than 45°. The pivot member 820 may be implemented using a rod or other suitable component that extends across the width of both the standing member 750 and base member 720, and that engages both the standing member 750 and the base member 720 at a vertex of angle α. The pivot member 820 may be rod-shaped, or the pivot member 820 may have any suitable shape for a cross-section. A locking mechanism (not shown) may be added to the system to permit locking the angle α during use of the system 700. The pivot member 820, the stand member 750 and/or the base member 720 may be configured to lock the angle α at selected angles using, for example, a ratcheting mechanism, a spring-loaded lever mechanism, or other similar mechanisms. In an example implementation, the pivot member 820 may include one or more detents or other similar locking mechanism at selected angles α. The pivot member 820 may then permit the standing member 750 to collapse onto the base member 720 thereby reducing the size of the system for storage purposes. In an example of such an implementation, the pivot member 820 includes a single detent at α=45°.

The present invention further comprises a method of vascular access that is safe, rapid, and repeatable, without the need for additional monitoring systems or extensive expertise, or in settings where conditions for practicing standard vascular access techniques, such as the Seldinger technique, may be impractical or impossible.

Generally, the method of vascular access comprises the steps of: 1) placing a vascular access system over an estimated location of a desired blood vessel of a patient; 2) advancing a plurality of access needles such that the plurality of access needles penetrate the tissue of the patient in the estimated location of the desired blood vessel; 3) observing an aspiration of blood from at least one of the needles, indicating said needle has accessed the desired blood vessel; 4) inserting a guidewire through the said needle and into the desired blood vessel; and 5) removing the vascular access system while maintaining the position of the guidewire.

In some embodiments, the estimated location of the desired blood vessel is determined by locating a pulse, placing a mark approximately where the pulse is located or noting landmarks relative to the approximate location of the pulse, and aligning the vascular access system with the mark or landmarks such that the vascular access system is centered over the estimated location of the desired blood vessel. Alternatively, a medical professional may align the vascular access system with known landmarks, such as bony landmarks, used for estimating the location of the desired blood vessel. The desired blood vessel may be an artery or a vein. In one embodiment, the vascular access system is used to obtain access to the femoral artery. In some other embodiments, the vascular access system may be used to obtain access to, without limitation, the radial artery, or other arteries as desired.

In further embodiments, the needles may be advanced in predetermined or preset increments.

In further embodiments, the method may further comprise the step of advancing a medical device over the guidewire and into the desired blood vessel. Said medical device may, without limitation, comprise: a sheath, a catheter, a pressure monitoring device, an occlusion device, a second wire, and/or the like.

Although a primary use of the vascular access system is to achieve access to major arteries, the system may also be used to achieve access to veins. The degree of blood aspiration when a needle accesses a vein will be less than when an artery is accessed. Access to a vein may be desired for placement of IVs, IV filters, and/or the like.

Figure 1:
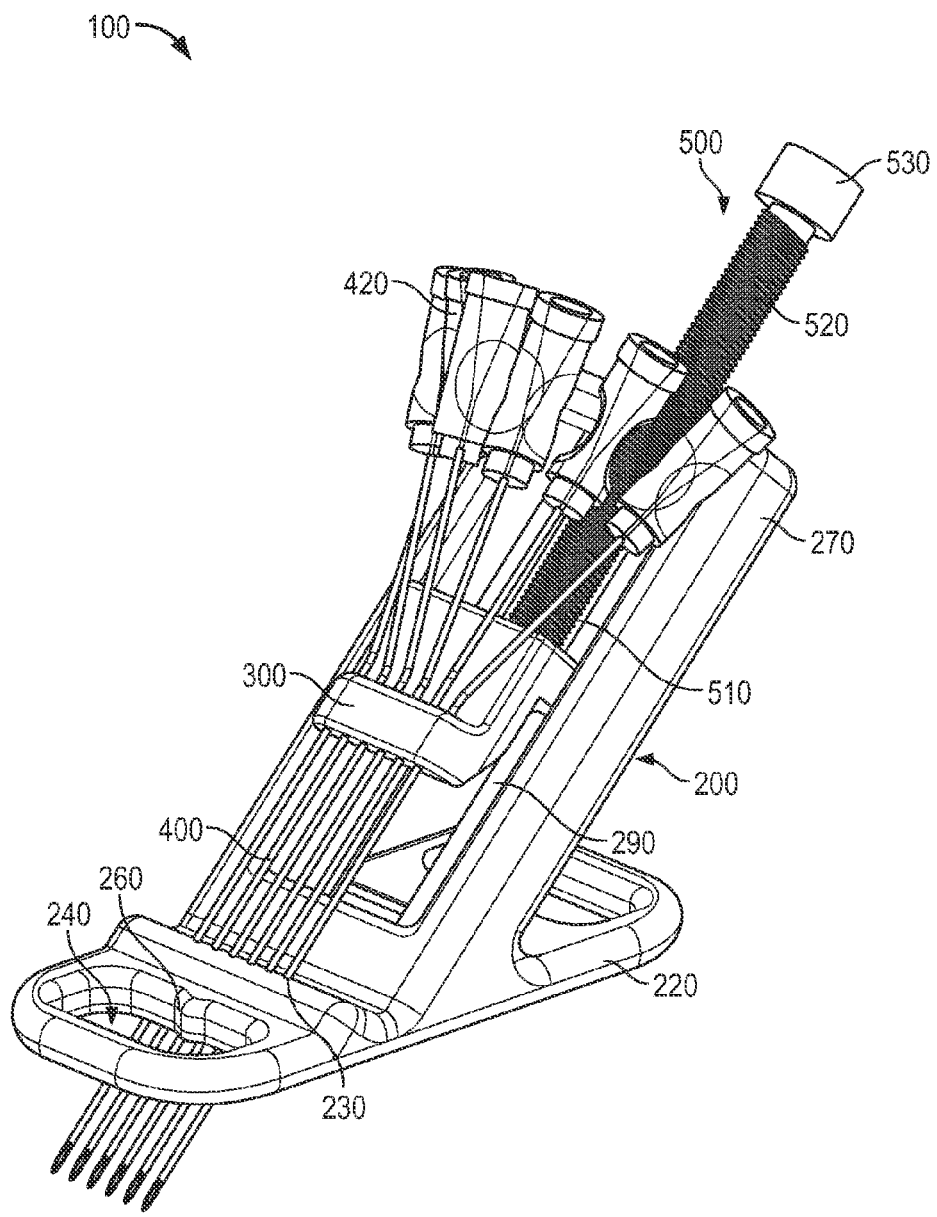
FIG. 1 is an isometric view of a particular screw drive embodiment of the vascular access system of the present invention.
Figure 4:
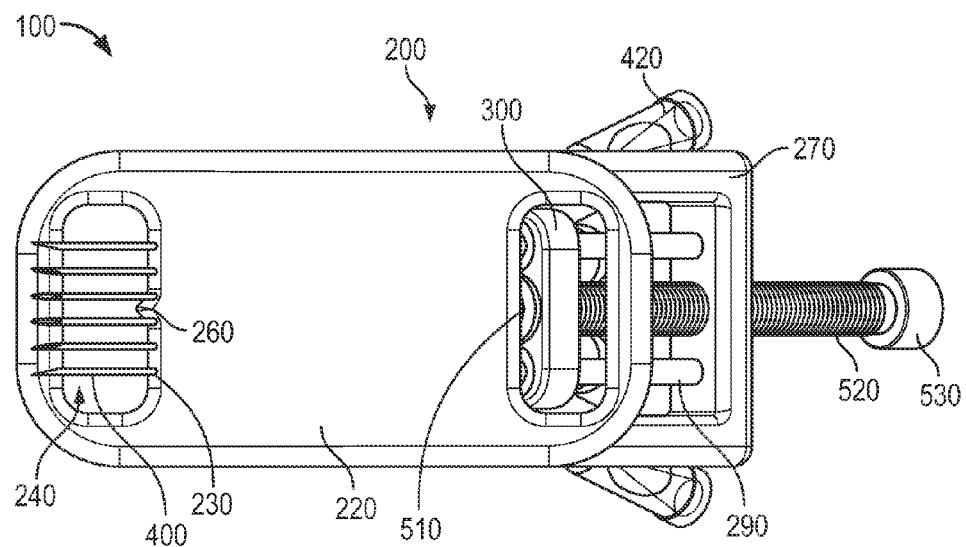
FIG. 4 is a bottom view of the embodiment of FIG. 1.
Figure 5:
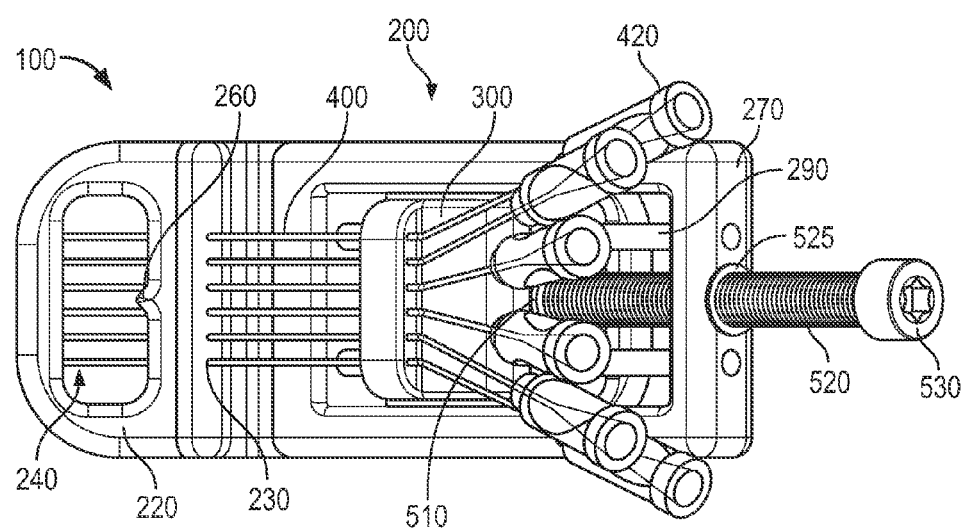
FIG. 5 is top view of the embodiment of FIG. 1.
Figure 6:
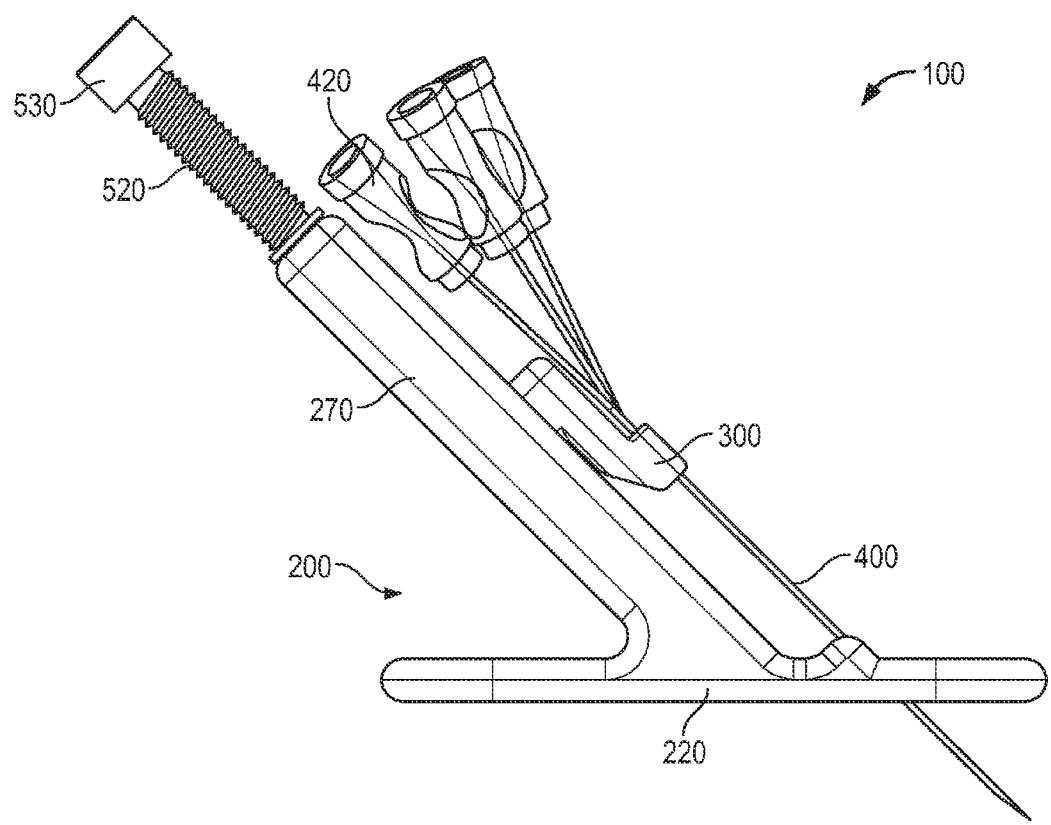
FIG. 6 is first side view of the embodiment of FIG. 1.
Figure 7:
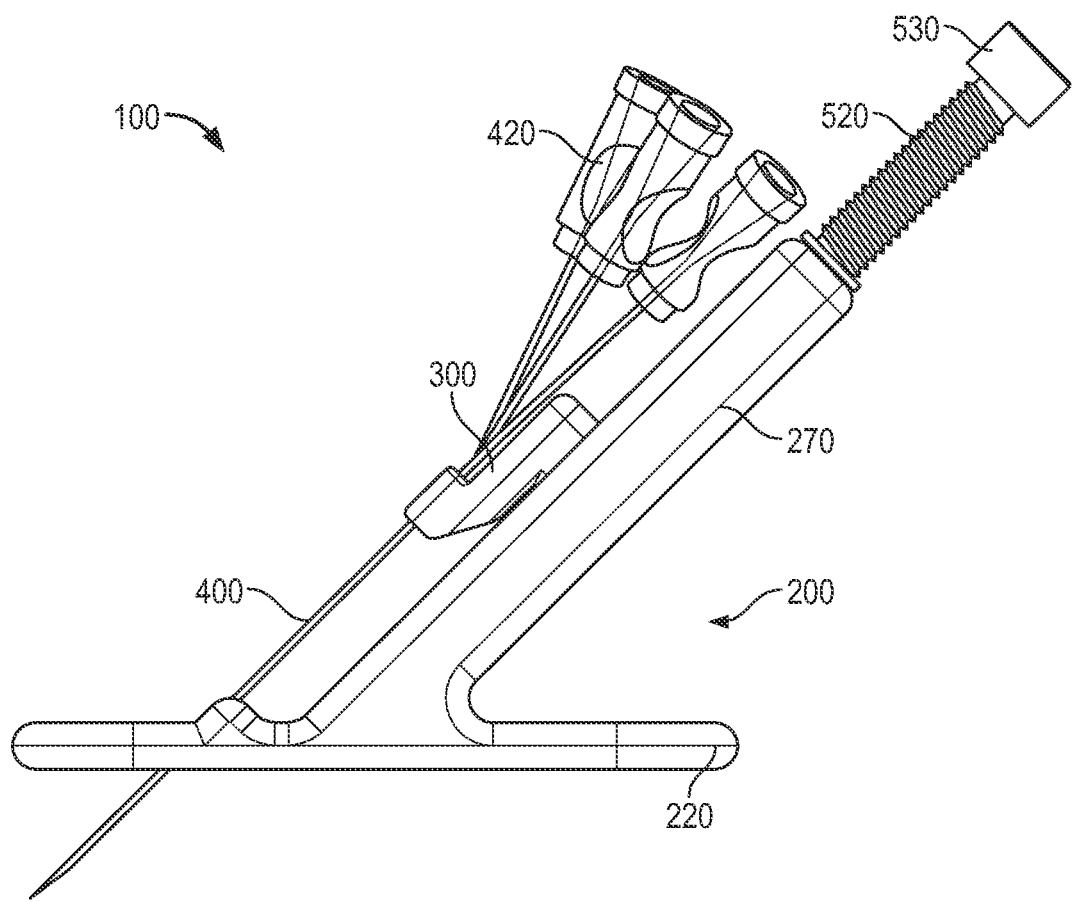
FIG. 7 is a second side view of the embodiment of FIG. 1.

Those of ordinary skill in the art will understand that the different features of the various embodiments described above may be used in example implementations of any of the other embodiments. For example, an example embodiment of the invention may include a control mechanism of the types described above with reference to FIGS. 1-10 and a pivot member 820 of the type described with reference to FIGS. 11-13. Similarly, an example embodiment of the invention may lack a control mechanism as described above with reference to FIGS. 11-13 and incorporate a body member that does not include a pivot member joining the base member to the stand member as shown in FIG. 1. Any of the embodiments explicitly described above may incorporate features explicitly described with reference to any other embodiment.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A vascular access system adapted to locate and provide access to a blood vessel without the need for additional monitoring or guidance systems, comprising:
    a. a body member comprising a base member and a stand member;
    b. a shuttle member movably coupled to the body member; and
    c. a plurality of hollow, blood vessel access needles parallel to one another, fixedly coupled to the shuttle member,
    wherein the shuttle member is advanceable along the body member in a controlled manner so that the hollow, blood vessel access needles parallel to one another are configured to simultaneously and evenly pierce skin of a patient with which the vascular access system is used until there is aspiration of blood sufficient from a blood vessel accessed by and through at least one of the needles to indicate vascular access to the blood vessel to locate and provide access to the blood vessel without the need for additional monitoring or guidance systems.

2. The vascular access system of claim 1, wherein the plurality of hollow, blood vessel access needles are evenly spaced from one another.

3. The vascular access system of claim 2, wherein the plurality of hollow, blood vessel access needles are spaced apart from one another by a distance of about 3 mm, about 4 mm, or about 5 mm.

4. The vascular access system of claim 1, wherein at least one of the plurality of hollow, blood vessel access needles further comprises a needle hub member.

5. The vascular access system of claim 1, wherein the base member and the stand member are integrally formed together.

6. The vascular access system of claim 1, wherein the stand member is coupled to the base member at an angle.

7. The vascular access system of claim 6, wherein the angle is about 45 degrees.

8. The vascular access system of claim 6, further comprising a pivot member joining the stand member and the base member at a vertex of the angle, the stand member being movably coupled to the base member at the pivot member to vary the angle.

9. The vascular access system of claim 8, wherein the base member further comprises at least one window portion located extending from a top surface of the base member to a bottom surface of the base member so that the patient's skin is visible through the window when the vascular access system is against the patient's skin.

10. The vascular access system of claim 1, wherein the base member further comprises at least one alignment element adapted to align a centrally located access needle with an estimated location of the blood vessel.

11. The vascular access system of claim 1, wherein the shuttle member is slidably coupled to the stand member.

12. The vascular access system of claim 1, wherein the body member further comprises at least one rail member, and the shuttle member is slidably coupled to the rail member.

13. The vascular access system of claim 1, further comprising a control assembly adapted to provide a controlled rate of advancement of the shuttle member relative to the body member.

14. The vascular access system of claim 13, wherein the control assembly further comprises a screw member, the screw member operably coupled to the shuttle member and the body member.

15. The vascular access system of claim 13, wherein the control assembly further comprises a ratchet mechanism operably coupled to the shuttle member and the body member.

16. The vascular access system of claim 15, wherein the ratchet mechanism comprises:
    a. a tension member operably coupled to the shuttle member and the body member; and
    b. an activator mechanism, wherein the activator mechanism permits a controlled, incremental advancement of the shuttle member.

17. The vascular access system of claim 1, further comprising a plurality of apertures disposed through the body member, the apertures configured to receive at least a portion of one of the plurality of hollow, blood vessel access needles within each of the apertures.

18. The vascular access system of claim 1, wherein the plurality of hollow, blood vessel access needles are aligned in a single row.

19. A vascular access system adapted to locate and provide access to a blood vessel without the need for additional monitoring or guidance systems, comprising:
    a. a body member;
    b. a shuttle member movably coupled to the body member;
    c. a plurality of hollow, blood vessel access needles parallel to one another and fixedly coupled to the shuttle member; and
    d. a control assembly operably coupled to the body member and the shuttle member, wherein the control assembly is adapted to provide a controlled rate of advancement of the shuttle member along the body member so that the hollow, blood vessel access needles parallel to one another are configured to simultaneously and evenly pierce skin of a patient with which the vascular access system is used until there is aspiration of blood sufficient from a blood vessel accessed by and through at least one of the needles to indicate vascular access to the blood vessel to locate and provide access to the blood vessel without the need for additional monitoring or guidance systems.

20. The vascular access system of claim 19, wherein the plurality of hollow, blood vessel access needles are aligned in a single row.

* * * * *